United States Patent [19]

Wood et al.

[11] Patent Number: 5,443,819
[45] Date of Patent: Aug. 22, 1995

[54] COMPOSITION AND METHOD OF ENHANCING SUN TANNING

[75] Inventors: John M. Wood; Karin U. Schallreuter, both of Quickborn, Germany

[73] Assignee: Stiefel Laboratories, Inc., Coral Gables, Fla.

[21] Appl. No.: 150,015

[22] PCT Filed: May 15, 1992

[86] PCT No.: PCT/GB92/00877

§ 371 Date: Nov. 15, 1993

§ 102(e) Date: Nov. 15, 1993

[87] PCT Pub. No.: WO92/20321

PCT Pub. Date: Nov. 26, 1992

[30] Foreign Application Priority Data

May 15, 1991 [GB] United Kingdom ............... 9110651

[51] Int. Cl.⁶ .................. A61K 7/021; A61K 7/42; A61K 7/44
[52] U.S. Cl. ...................... 424/59; 424/60; 424/63
[58] Field of Search ................ 424/59, 63, 60

[56] References Cited

U.S. PATENT DOCUMENTS

| | | |
|---|---|---|
| 4,129,644 | 12/1978 | Kalopissis et al. ............ 424/59 |
| 4,349,536 | 9/1982 | Hausler ........................ 424/59 |
| 4,743,442 | 5/1988 | Raaf et al. .................... 424/47 |
| 4,806,344 | 2/1989 | Gaskin ......................... 424/59 |

FOREIGN PATENT DOCUMENTS

| | | |
|---|---|---|
| 0155344A2 | 9/1985 | European Pat. Off. ........ A61K 7/48 |
| 0380335A2 | 8/1990 | European Pat. Off. ........ A61K 7/42 |
| 0424033A2 | 4/1991 | European Pat. Off. ........ A61K 7/48 |
| 2287899 | 10/1975 | France ......................... 424/59 |
| 2108612 | 4/1990 | Japan ........................... A61K 7/00 |

OTHER PUBLICATIONS

Kono et al., *Chemical Abstracts*, 114(21):202133d, 2(1), pp. 18-26 (1990).

*Primary Examiner*—Dale R. Ore
*Attorney, Agent, or Firm*—Mathews, Woodbridge & Collins

[57] ABSTRACT

The present invention relates to the enhancement of suntanning following exposure to sunlight or other source of UV light by topically applying pseudocatalase compounds.

15 Claims, No Drawings

COMPOSITION AND METHOD OF ENHANCING SUN TANNING

This application of the notional stage of PCT/GB0-877 filed May 15, 1992.

The present invention relates to the enhancement of sun tanning and has particular, but not exclusive, application to the sun tanning of fair skin (ie. Types I and II skins).

The extent of sun tanning following exposure to sunlight or other source of UV light depends upon the type of skin. Those with fair skin (ie. Types I and II) do not readily tan and are much more liable to sunburn than those with dark skin (ie. Types IV and V). Existing sunscreen preparations protect against sunburn but do not enhance tanning compared with the unprotected skin.

It has now surprisingly been found that tanning can be enhanced by topical application of manganese (II) bicarbonate or other pseudocatalases.

We have disclosed in a co-pending Patent Application of the same priority and filing dates and corresponding to UK Patent Application No. 9110652 that pseudocatalase can be used topically to treat vitiligo.

By pseudocatalase, we mean a plasma membrane permeable physiologically acceptable compound which catalyzes the dismutation of $H_2O_2$ in vivo in analogous manner to catalase.

Exposure of the skin to UVB radiation generates superoxide anion radicals which is a preferred substrate for human tyrosinase (40 times better than oxygen) thereby promoting melanin formation. However, the superoxide anion radicals are dismutated into dioxygen and peroxide ion causing an undesirable increase in hydroxyl ion concentration unless catalase or some other competing mechanism removes peroxide ion. Thus, the presence of a pseudocatalase is believed to allow sufficient UVB exposure for superoxide anion radical formation to promote pigmentation in catalase deficient areas without burning or other cell damage.

According to a first aspect of the present invention, there is provided the use of a pseudocatalase in the manufacture of a topical composition for the enhancement of tanning of skin, especially fair skin, on exposure to sunlight or UVB light.

In a second aspect, the invention provides a topical sunscreen composition comprising a pseudocatalase, a sunscreen agent and a physiologically acceptable topical vehicle therefor.

In a third aspect, the invention provides a pseudocatalase for use in the enhancement of tanning of skin, especially fair skin, on exposure to sunlight or UVB light.

In a fourth aspect, the invention provides a method of enhancing tanning of skin, especially fair skin, which comprises applying to the skin an effective amount of a pseudocatalase.

In a fifth aspect, the invention provides use of a pseudocatalase to enhance tanning of skin on exposure to sunlight or UVB light.

The pseudocatalase can be any physiologically acceptable compound which catalyzes the dismutation of hydrogen peroxide. Some compounds such as Mn(II) bicarbonate are already known to be pseudocatalases and others can be determined by simple screening tests.

The presently preferred pseudocatalases are transition metal co-ordination complexes in which the inductive effect of the electron acceptor ligand enhances the redox effect of the metal on hydrogen peroxide dismutation. Usually, the metal will be Cu(I), Fe(II) or, especially Mn(II) and the ligand will be bicarbonate. It is especially preferred that the pseudocatalase is Mn(II) bicarbonate complex. Said complex readily can be prepared by contacting manganous chloride with excess bicarbonate in aqueous solution.

The pseudocatalase is formulated in a topical vehicle for use. Conveniently, the vehicle comprises a hydrophilic cream to which an aqueous solution or suspension of the pseudocatalase is added to form a cream or lotion. Alternatively, the vehicle can be a bath oil although any other compatible topical vehicle can be used to provide a topical composition.

Usually, the composition will contain a sunscreen agent and other components such as emollients, perfumes etc conventionally used in sunscreen preparations. In particular, the composition can contain calcium ions, suitably added as calcium chloride, usually in a concentration of 5 to 20 millimolar. Subject to compatibility with the pseudocatalase and superoxide anion, any conventional sunscreen agent, such as Parsol MCX, or other component can be used.

The invention is illustrated in the following non-limiting Examples.

EXAMPLE 1

Manganous chloride (380 mg) was added to a solution of sodium bicarbonate (2.3 g) in purified water (3.0 ml) at ambient temperature. The mixture was allowed to stand until the evolution of gas had ceased. The resultant pinkish brown liquid was mixed with a hydrophilic cream (Neribase) to provide a white cream.

Neribase is a cream vehicle containing Macrogol stearate 2000; stearic alcohol; liquid paraffin; white soft paraffin; polyacrylic acid; sodium hydroxide; disodium EDTA (i.e. ethylenediaminetetraacetic acid disodium salt); methyl and propyl Paraben (i.e. 4-hydroxybenzoic acid methyl and propyl esters); and water.

The cream was applied to test skin areas of healthy volunteers having skin type II or III and, after a period of 20, 45 or 60 minutes, the treated skin exposed to UVB light for 10 to 20 seconds. The UVB source was a Saalmann UV-Test machine and the doses were 0.06, 0.05, 0.04, 0.03, 0.02 $mJ/cm^2$ (10 seconds) and 0.18, 0.15, 0.12, 0.09, 0.06 $mJ/cm^2$ (30 seconds). The degree of erythema/tanning of the treated area and untreated area was determined by observation after 24 and 72 hours post-irradiation.

The results are set forth in Table I below. The erythema increase is indicated on the scale +, ++ and +++ with ++ and +++ presenting a darker tan.

TABLE I

| Sex/age | Skin type | $T_1$ min | $T_2$ sec | 24 h treated/control side | 72 h treated/control side |
|---|---|---|---|---|---|
| M/27 | III | 20 | 10 | no difference | no difference |
| F/22 | III | 20 | 10 | +++/+ | ++/+ |
| F/25 | III | 20 | 10 | +++/++ | ++/+ |
| F/23 | III | 20 | 10 | +++/++ | +++/+ |
| M/30 | III | 20 | 10 | +++/++ | ++/+ |
| M/23 | III | 20 | 10 | ++/+++ | no difference |
| M/24 | III | 20 | 10 | +/++ | no difference |
| F/25 | II | 20 | 10 | +++/++ | ++/+ |
| F/28 | II | 20 | 10 | +++/++ | ++/++ |

+-+++: grade of erythema/tanning
$T_1$ = time between application and UVB irradiation
$T_2$ = time of UVB irradiation

EXAMPLE 2

The test of Example 1 was repeated using creams to which calcium chloride had been added to provide 5 millimolar or 10 mmole calcium ion content. The results are set forth in Tables II and III below.

TABLE II (5 mmol $Ca^{2+}$)

| Sex/age | Skin type | $T_1$ min | $T_2$ sec | 24 h treated/control side | 72 h treated/control side |
|---|---|---|---|---|---|
| F/26 | III | 20 | 10 | +++/++ | ++/+ |
| M/52 | III | 20 | 10 | +++/++ | ++/+ |
| F/21 | III | 20 | 10 | ++/+++ | +/++ |
| F/22 | III | 20 | 10 | ++/+++ | +/++ |
| M/27 | III | 40 | 10 | +/++ | +/++ |
| F/25 | III | 20 | 30 | +++/++ | ++/++ |
| F/27 | III | 20 | 30 | no difference | +/++ |
| F/28 | III | 60 | 30 | ++/+++ | +/++ |
| F/19 | II | 20 | 10 | ++/+++ | +/+++ |
| M/32 | II | 20 | 10 | +/++ | +/++ |
| F/43 | II | 45 | 10 | +++/++ | +++/++ |
| M/21 | II | 45 | 10 | ++/+ | ++/+ |
| M/27 | II | 60 | 10 | no difference | no difference |
| M/30 | II | 20 | 30 | +++/++ | +++/++ |
| M/33 | II | 20 | 30 | +++/++ | ++/+ |

+-+++: grade of erythema/tanning
$T_1$ = time between application and UVB irradiation
$T_2$ = time of UVB irradiation

TABLE III (10 mmol $Ca^{2+}$)

| Sex/age | Skin type | $T_1$ min | $T_2$ sec | 24 h treated/control side | 72 h treated/control side |
|---|---|---|---|---|---|
| F/27 | III | 20 | 10 | +/++ | +/++ |
| M/50 | III | 20 | 10 | +++/++ | ++/+ |
| F/21 | III | 20 | 10 | +++/++ | ++/+ |
| F/22 | III | 20 | 10 | no difference | no difference |
| F/23 | II | 20 | 10 | no difference | no difference |
| F/49 | II | 20 | 10 | +/++ | no difference |
| M/25 | II | 20 | 10 | ++/+ | +++/++ |
| F/47 | II | 45 | 10 | +++/++ | +++/++ |
| M/24 | II | 45 | 10 | ++/+ | ++/+ |
| M/25 | II | 45 | 10 | ++/+++ | +/++ |

+-+++: grade of erythema/tanning
$T_1$ = time between application and UVB irradiation
$T_2$ = time of UVB irradiation

We claim:

1. A topical composition for enhancing tanning of the skin, comprising: an effective amount of a pseudocatalase; an effective amount of a sunscreen agent; and a physiologically acceptable topical vehicle, wherein the pseudocatalase is a transition metal bicarbonate complex.

2. The composition according to claim 1, wherein the composition is free of calcium ions.

3. The composition according to claim 1, wherein the composition contains 5 to 20 millimolar calcium ions.

4. The composition according to claim 1, wherein the transition metal is selected from the group consisting of Cu(I), Fe(II), and Mn(II).

5. The composition according to claim 5, wherein the complex is a Mn(II)-bicarbonate complex.

6. The composition according to claim 5, wherein the Mn(II)-bicarbonate complex has been obtained by contacting manganous chloride with excess sodium bicarbonate in aqueous solution.

7. A method of enhancing tanning of skin which comprises applying to the skin an effective amount of a pseudocatalase, wherein the pseudocatalase is a transition metal bicarbonate complex.

8. The method according to claim 7, which further comprises exposing pseudocatalase-treated skin to sunlight or UVB light.

9. The method according to claim 7, wherein the pseudocatalase is admixed with a physiologically acceptable topical vehicle.

10. The method according to claim 7 wherein the transition metal is selected from the group consisting of Cu(I), Fe(II), and Mn(II).

11. The method according to claim 10 wherein the complex is Mn(II)-bicarbonate complex.

12. The method according to claim 11 wherein the Mn(II) bicarbonate complex is obtained from contacting manganous chloride with excess sodium bicarbonate in aqueous solution.

13. The method according to claim 7 wherein the pseudocatalase is admixed with an effective amount of a sunscreen agent.

14. The method according to claim 7 wherein the pseudocatalase is applied as a composition free of calcium ions.

15. The method according to claim 7 wherein the pseudocatalase is applied as a composition containing 5 to 20 millimolar calcium ions.

* * * * *